(12) United States Patent
Johansen et al.

(10) Patent No.: US 7,938,023 B2
(45) Date of Patent: *May 10, 2011

(54) WET-GAS FLOWMETER

(75) Inventors: Espen S. Johansen, Humble, TX (US); Omer Haldun Unalmis, Kingwood, TX (US); John Lievois, Houston, TX (US)

(73) Assignee: Weatherford/Lamb Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/698,772

(22) Filed: Feb. 2, 2010

(65) Prior Publication Data

US 2010/0138169 A1 Jun. 3, 2010

Related U.S. Application Data

(63) Continuation of application No. 11/625,460, filed on Jan. 22, 2007, now Pat. No. 7,654,155.

(60) Provisional application No. 60/826,180, filed on Sep. 19, 2006.

(51) Int. Cl.
*G01F 1/44* (2006.01)

(52) U.S. Cl. .................................................. 73/861.63

(58) Field of Classification Search ............... 73/861.63, 73/861.64; 702/49, 47
See application file for complete search history.

(56) References Cited

U.S. PATENT DOCUMENTS 7,654,155 B2 * 2/2010 Johansen et al. ........... 73/861.63
* cited by examiner

*Primary Examiner* — Jewel Thompson
(74) *Attorney, Agent, or Firm* — Patterson & Sheridan, L.L.P.

(57) ABSTRACT

Methods and apparatus determine phase fractions for phases within a fluid mixture flow under a wide range of flow conditions including wet-gas flow. Appropriate flow algorithms can utilize this phase fraction information with a total flow rate of the mixture to find individual flow rates for phases, such as oil, water, and gas or gas and liquid, which can represent a combination of oil and water phases. For some embodiments, a multiphase flowmeter includes an array of spatially distributed pressure sensors configured to determine a velocity of the mixture flow and hence the total flow rate, which is applied with information from a differential pressure meter to calculate the bulk density of the fluid mixture. Further, additional speed of sound information or a water-in-liquid ratio as may be determined by spectral analysis can enable differentiation between the oil and water phases.

20 Claims, 7 Drawing Sheets

WET-GAS FLOWMETER

CROSS-REFERENCE TO RELATED APPLICATIONS

This is a continuation of U.S. patent application Ser. No. 11/625,460 filed Jan. 22, 2007, now U.S. Pat. 7,654,155, which claims benefit of U.S. Provisional Patent Application Ser. No. 60/826,180 filed Sep. 19, 2006, which are herein incorporated by reference.

BACKGROUND OF THE INVENTION

1. Field of the Invention

Embodiments of the invention generally relate to methods and apparatus for determining phase fractions and/or flow rates of fluid flow.

2. Description of the Related Art

In the petroleum industry, as in many other industries, ability to monitor flow of fluids in process pipes in real time offers considerable value. Oil and gas operators measure individual water/oil/gas flow rates within an overall production flow stream containing a mixture of these three phases. This information is used to improve well production, allocate royalties, prevent corrosion based on the amount of water and determine the well's performance.

Production from gas wells can include a significant liquid content (water, hydrocarbon oil, condensate or combinations thereof). Flows with relatively high gas amounts with respect to liquid amounts (e.g., around or below 5% liquid by volume) are described as wet-gas flows and represent the high gas-volume-fraction (GVF) end of multiphase flows. Various prior flowmeters attempt to enable flow rate measurements or determinations of these high-GVF flows unsuccessfully due to factors such as low accuracy and certainty in the flow rate results. Further, prior approaches often require application of generic correlation methods to correct measurements, and complex and expensive configurations for the flowmeters.

Therefore, there exists a need for improved methods and apparatus that enable determining individual flow rates within a multiphase fluid flow. A further need exists for a flowmeter to measure wet-gas flow with improved uncertainty and accuracy.

SUMMARY OF THE INVENTION

The invention generally relates to methods and apparatus for determining phase fractions within a fluid mixture flow under a wide range of flow conditions including wet-gas flow. Appropriate flow algorithms can utilize this phase fraction information with a total flow rate of the mixture to find individual flow rates for phases, such as oil, water, and gas or gas and liquid, which can represent a combination of oil and water phases. For some embodiments, a multiphase flowmeter includes an array of spatially distributed pressure sensors configured to determine a velocity of the mixture flow and hence the total flow rate, which is applied with information from a differential pressure meter to calculate the bulk density of the fluid mixture. Further, additional speed of sound information or a water-in-liquid ratio can enable differentiation between the oil and water phases.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the invention relate to multiphase flowmeters capable of determining phase fractions within a multiphase fluid mixture under a broad range of flow conditions such as wet-gas flow. Combining this phase fraction information with a total combined flow rate of the fluid mixture determined based on a sensed velocity of the fluid mixture through a given area enables resolving flow rates for the phase fractions. The phase fractions and hence phase flow rates determined can include oil, gas, and water phases individually or gas and liquid (e.g., oil/water) phases.

Figure 1:
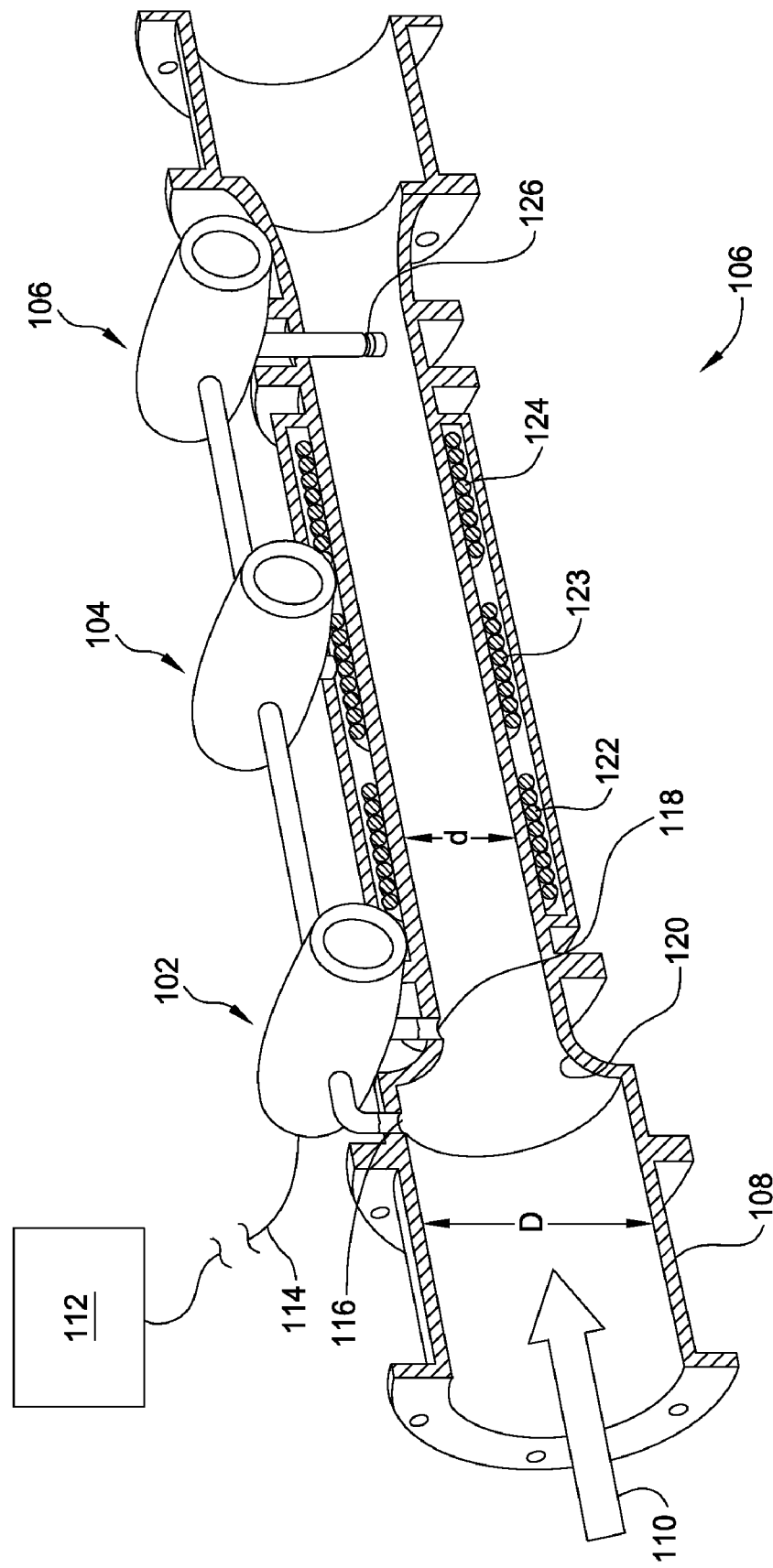
FIG. 1 is a partial cross section view of a flow rate measuring system according to embodiments of the invention, including a differential pressure based meter, a spatially distributed pressure sensor (Sonar) based meter and an optional water-in-liquid ratio meter all disposed along a conduit containing a fluid flow.

FIG. 1 illustrates a flow rate measuring system 100 including a Venturi-based meter 102, a pressure sensor array (Sonar) based meter 104, and an optional water-in-liquid ratio (WLR) meter 106, all disposed along a conduit 108 containing a fluid flow 110 as depicted by an arrow. The meters 102, 104, 106 couple to signal interface circuitry 112 through a transmission line 114. The signal interface circuitry 112 receives and processes signals from two or more of the meters 102, 104, 106 to calculate phase fraction flow rates of fluid flow 110 using logic based on principals described further herein (see FIGS. 2-4).

Various differential pressure devices utilize a flow nozzle (e.g., the Venturi-based meter 102), an orifice plate or V-cone to produce changes in velocity and pressure of the fluid flow 110 according to conservation of energy and mass as the fluid flow 110 passes through such devices. Any of these differential pressure devices can therefore provide a differential pressure measurement suitable for applying in equations relating to the conservation of energy and mass in order to determine a property, such as density, of the fluid flow 110. Calculations shown hereinafter refer to the Venturi-based meter 102 as an example way to determine the density while similar modified equations can derive the same results with other ones of the differential pressure devices.

The Venturi-based meter 102 includes first and second ports 116, 118 exposed to pressures of the fluid flow 110 that traverses a constriction formed by a converging inner diameter portion 120 of the conduit 108. As a further example of a different type of flow nozzle, the inner diameter can diverge in some embodiments instead of converge to create a measurable pressure difference. The Venturi-based meter 102 defines a differential pressure sensing meter between the first port 116 disposed upstream of the converging inner diameter portion 120 and the second port 118 located in a throat section downstream of the converging inner diameter portion 120.

The Sonar-based meter 104 can include first, second and third pressure sensing elements 122, 123, 124 distributed along a length of the conduit 108. Spacing between the sensing elements 122-124 enables sensing short duration local pressure variations traveling with the fluid flow (referred to as "flow velocity sensing") and can also enable sensing acoustic signals traveling at the speed of sound through the fluid flow 110 within the conduit 108 (referred to as "acoustic sensing"). For some embodiments, coils of optical fiber wrapped around the conduit 108 define each of the sensing elements 122-124. Other pressure measuring devices such as piezoelectric or polyvinylidene fluoride (PVDF) based detectors can provide pressure time-varying signals with the Sonar-based meter 104. The acoustic signals and/or the local pressure variations can originate from naturally occurring phenomenon as the fluid flow 110 travels through the conduit 108.

Regardless of the type of the sensing elements 122-124 utilized, interpretation of these signals from the Sonar-based meter 104 enables determination of at least the mixture flow velocity ($v_m$) of the fluid flow 110. For some embodiments, interpreting the signals from the Sonar-based meter 104 permits determination of the speed of sound (SOS, $a_{mix}$) of the fluid flow 110. U.S. Pat. Nos. 6,354,147 and 6,782,150, which are herein incorporated by reference, describe examples of appropriate calculations for determining the $a_{mix}$ and the velocity with similar apparatus that are suitable examples of the Sonar-based meter 104 with the sensing elements 122-124.

The WLR meter 106 can operate based on principles of spectroscopy by relying on differences in absorption between oil and water of near infrared light. In some embodiments, an intrusive probe of the WLR meter 106 within the fluid flow 110 provides a sample region 126 in which input light passes through a portion of the fluid flow 110 and is detected thereafter. Absorption of the input light by the fluid flow 110 attenuates the input light and depends in a wavelength conditioned manner on the contents of the fluid flow 110. As a suitable example of the WLR meter 106, U.S. Patent Publication No. 2006/0186340 and U.S. patent application Ser. No. 11/625,427 (WEAT/0641.P1), which are herein incorporated by reference, describe an infrared optical fiber system capable of determining, for example, the percentage of water and the percentage of oil.

Figure 2:
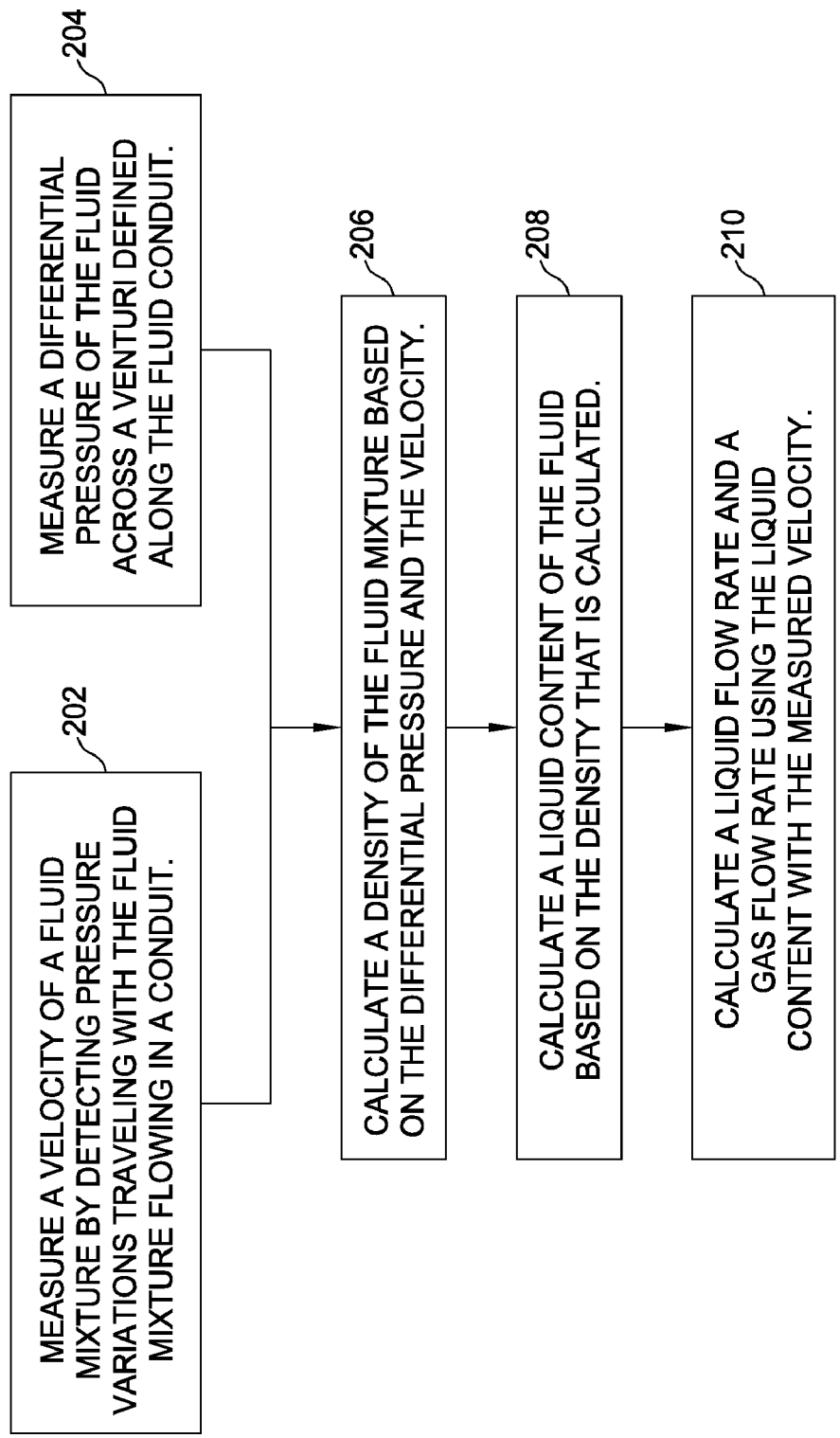
FIG. 2 is a flow chart illustrating use of the differential pressure based meter and the Sonar-based meter to calculate a liquid flow rate and a gas flow rate, according to embodiments of the invention.

FIG. 2 shows a flow chart illustrating use of the Venturi-based meter 102 and the Sonar-based meter 104 to calculate a liquid flow rate and a gas flow rate. At velocity measurement step 202, data including a Sonar velocity ($v_S$) obtained from the Sonar-based meter 104 enables determining a mixture flow velocity ($v_m$) of the fluid flow 110. In operation, the Sonar-based meter 104 detects pressure variation signals traveling with the fluid flow 110 to measure the Sonar velocity ($v_S$). The velocity measurement step 202 can include data processing beginning by calculating a throat Reynolds ($Re_d$) number as:

$$Re_d = \frac{\rho_g v_S d}{\mu_g}, \quad \text{(Equation 1)}$$

where $\rho_g$ is known gas density, d is a diameter of the conduit 108 along a throat section at which the Sonar-based meter 104 is disposed, and $\mu_g$ is known viscosity of gas. Using the throat Reynolds number ($Re_d$) and the Sonar velocity ($v_S$) that is measured enables calculation of the mixture flow velocity ($v_m$) according to:

$$v_m = v_S(1+C_0+C_1 Re_d^{-C_2})^{-1} \quad \text{(Equation 2),}$$

where $C_0$, $C_1$, $C_2$ are sonar calibration coefficients. The mixture flow velocity ($v_m$) is typically 1-5% lower than the measured Sonar velocity ($v_S$).

A differential pressure measurement occurs at differential pressure step 204 using the Venturi-based meter 102. Density step 206 calculates a mixture density ($\rho_m$) of the fluid flow 110 utilizing the differential pressure measurement from step 204 plugged into an algorithm such as follows based on conservation of energy and mass equations given a total flow rate ($Q_t$) determined by the flow velocity ($v_m$) from step 202. As a prerequisite to determining the total flow rate ($Q_t$), calculation of the extended throat area ($A_t$) occurs next using:

$$A_t = \pi \frac{d^2}{4}. \quad \text{(Equation 3)}$$

Multiplying the results from Equations 2 and 3 yields the total flow rate ($Q_t$) defined by:

$$Q_t = v_m A_t \quad \text{(Equation 4).}$$

Thereafter, the algorithm proceeds in setting up a final calculation for the density step 206 as represented by forthcoming Equation 12. First, calculation of a Venturi diameter ratio ($\beta$) includes:

$$\beta = \frac{d}{D}, \quad \text{(Equation 5)}$$

where D is a diameter of the conduit 108 at an inlet of the Venturi-based meter 102. Second, calculation of a velocity of approach factor (E) entails:

$$E = (1-\beta^4)^{-0.5} \quad \text{(Equation 6).}$$

Third, calculation of a pressure ratio ($\tau$) at the inlet and the throat includes:

$$\tau = \frac{P_2}{P_1} = \frac{P_S - \Delta P}{P_S}, \quad \text{(Equation 7)}$$

where $P_1$ is pressure at the first port 116, $P_2$ is pressure at the second port 118, $P_S$ is static pressure, and $\Delta P$ is the differential pressure. Fourth, a dry-gas Reynolds number ($Re_D$) based on inlet diameter differs from the throat Reynolds number ($Re_d$) by factor $\beta$ according to:

$$Re_D = Re_d \beta \quad \text{(Equation 8).}$$

Fifth, calculation of a dry-gas discharge coefficient (valid for ISA 1932 Nozzle as an example) involves:

$$C_d = 0.9900 - 0.2262\beta^{4.1} - (0.00175\beta^2 - 0.0033\beta^{4.15})(1\cdot 10^6 Re_D^{-1})^{1.15} \quad \text{(Equation 9)}.$$

Sixth, calculation of a fluid expansibility coefficient ($\epsilon$) refers to the isentropic expansion of gas at a change in pressure as defined by:

$$\varepsilon = \left[\left(\frac{\kappa\tau^{\frac{2}{\kappa}}}{\kappa-1}\right)\left(\frac{1-\beta^4}{1-\beta^4\tau^{\frac{2}{\kappa}}}\right)\left(\frac{1-\tau^{\frac{\kappa-1}{\kappa}}}{1-\tau}\right)\right]^{0.5}, \quad \text{(Equation 10)}$$

where $\kappa$ is a known gas isentropic coefficient. Seventh, calculation of a dry gas flow coefficient ($K_g$) includes:

$$K_g = C_d E\epsilon \quad \text{(Equation 11)}.$$

Eighth, calculation of the mixture density ($\rho_m$) from conservation of energy equation provides:

$$\rho_m = 2\Delta P\left(\frac{K_g A_t}{Q_t}\right)^2. \quad \text{(Equation 12)}$$

At liquid fraction determination step 208, using the mixture density ($\rho_m$) as determined in Equation 12 by inputting the velocity information (i.e., step 202) from the Sonar-based meter 104 with the response (i.e., step 204) from the Venturi-based meter 102 enables calculating the liquid content (liquid holdup, HL) as follows:

$$HL = \frac{\rho_m - \rho_g}{\rho_l - \rho_g}, \quad \text{(Equation 13)}$$

where the gas density ($\rho_g$) and a liquid density ($\rho_l$) are known or approximated values. An output step 210 includes calculating from results in Equations 4 and 13 a liquid flow rate ($Q_l$) and a gas volume flow rate (GVF, $Q_g$) using the following equations:

$$Q_l = HL Q_t \quad \text{(Equation 14)}$$

$$Q_g = (1-HL)Q_t \quad \text{(Equation 15)}.$$

Figure 3:
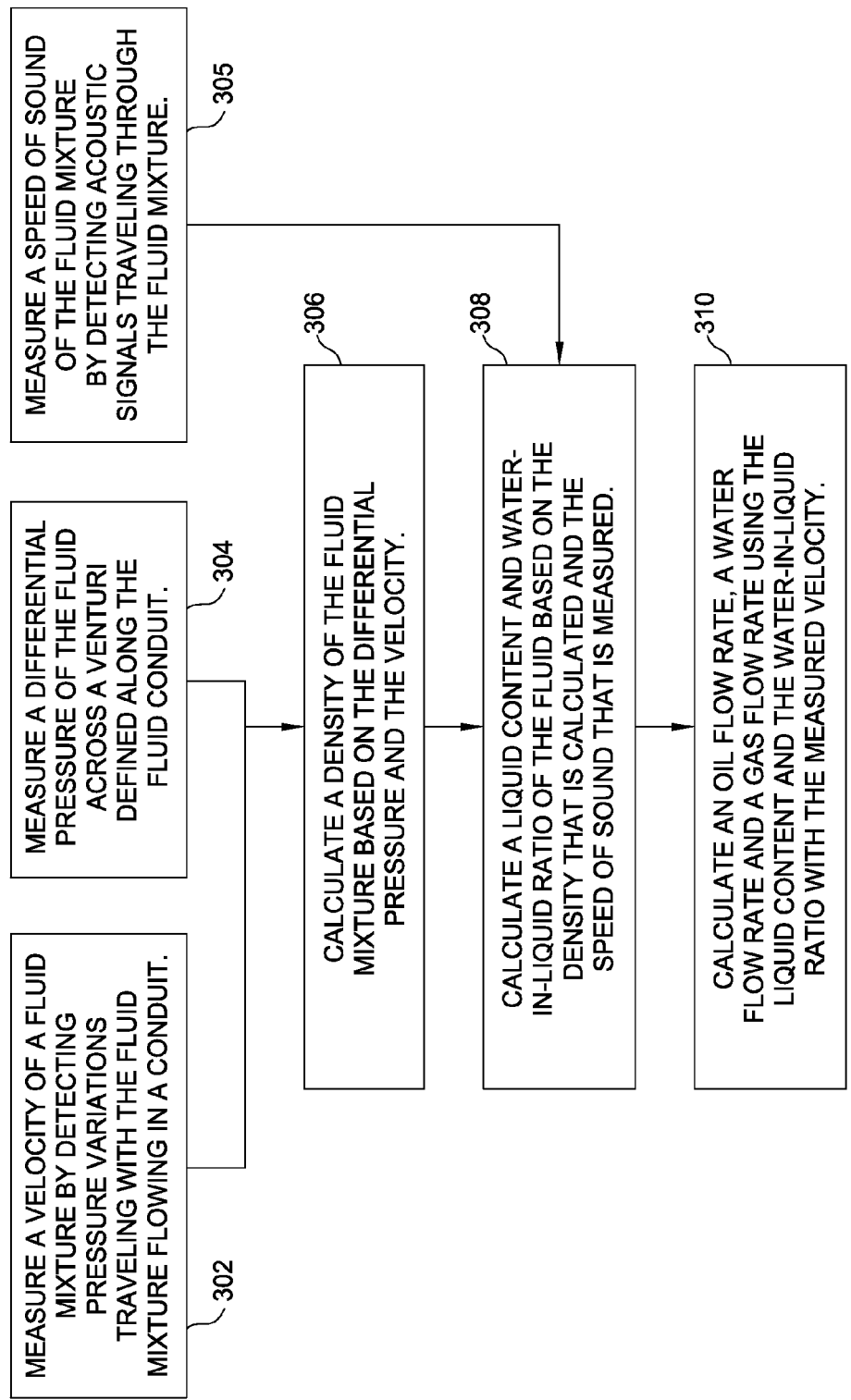
FIG. 3 is a flow chart illustrating use of the differential pressure based meter and the Sonar-based meter to calculate individual flow rates for gas, water and oil, according to embodiments of the invention.

FIG. 3 illustrates a flow chart showing use of the Venturi-based meter 102 and the Sonar-based meter 104 to calculate individual flow rates for gas, water and oil. At velocity measurement step 302, data obtained from the Sonar-based meter 104 enables determining a mixture flow velocity ($v_m$) of the fluid flow 110 and hence a total flow rate ($Q_t$) as previously described. A differential pressure measurement occurs at differential pressure step 304 using the Venturi-based meter 102. Like the approach shown in FIG. 2, density step 306 calculates a mixture density ($\rho_m$) of the fluid flow 110 utilizing the differential pressure measurement from step 304 in combination with the flow velocity ($v_m$) from step 302.

In addition to the mixture flow velocity ($v_m$), the Sonar-based meter 104 measures at SOS step 305 a SOS of the fluid flow 110. At liquid fraction determination step 308, using the mixture density ($\rho_m$) and SOS enables solving for liquid content (liquid holdup, HL) and water-in-liquid ratio (WLR) using the following two equations having these two values as the only unknowns:

$$a_{mix} = \left[\begin{array}{l}(HL)(1-WLR)\frac{\rho_m}{\rho_o a_o^2} + \\ (HL)(WLR)\frac{\rho_m}{\rho_w a_w^2} + \\ (1-HL)\frac{\rho_m}{\rho_g a_g^2} + \rho_m \frac{d}{Et}\end{array}\right]^{-1/2} \quad \text{(Equation 16)}$$

$$\rho_m = (1-WLR)(HL)\rho_o + (WLR)(HL)\rho_w + (1-HL)\rho_g, \quad \text{(Equation 17)}$$

where $\rho_o$, $\rho_w$ and $\rho_g$ are known densities of oil, water and gas, respectively, $a_o$, $a_w$ and $a_g$ are a known speed of sound of oil, water and gas, respectively, d is a diameter of the conduit, E is the Young's modulus for the material of the conduit 108, and t is a wall thickness of the conduit 108. Upon determining the liquid content (HL) and the water-in-liquid ratio (WLR), an output step 310 includes calculating an oil flow rate ($Q_o$), a water flow rate ($Q_w$), and a gas volume flow rate (GVF, $Q_g$) using Equation 15 above and the following equations:

$$Q_o = (1-WLR)(HL)Q_t \quad \text{(Equation 18)}$$

$$Q_w = WLR(HL)Q_t \quad \text{(Equation 19)}.$$

Figure 4:
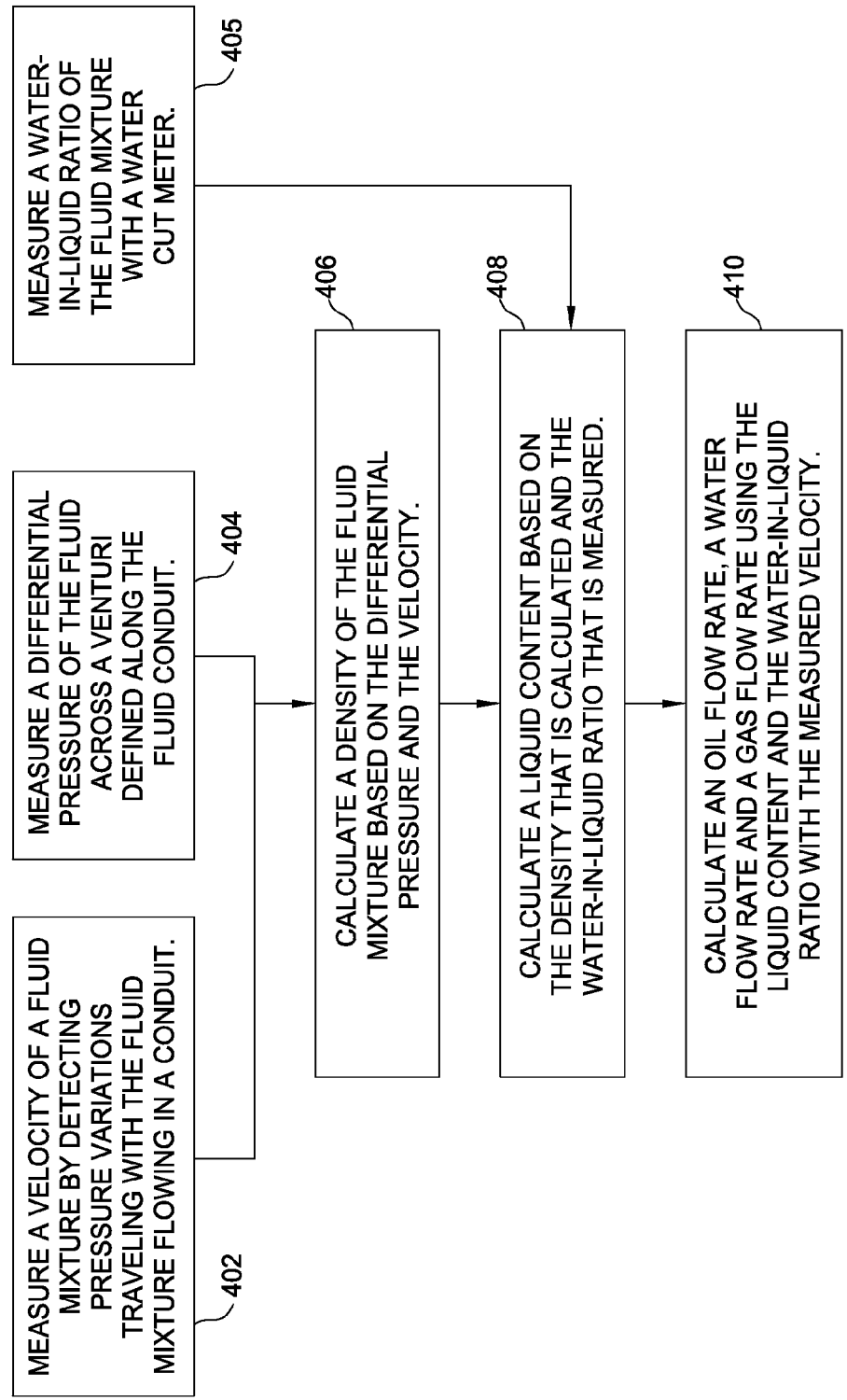
FIG. 4 is a flow chart illustrating use of the flow rate measuring system to calculate individual flow rates for gas, water and oil, according to embodiments of the invention.

FIG. 4 shows a flow chart illustrating use of all the meters 102, 104, 106 of the flow rate measuring system 100 to calculate individual flow rates for gas, water and oil. As previously described, data obtained at velocity measurement step 402 from the Sonar-based meter 104 enables determining a mixture flow velocity ($v_m$) of the fluid flow 110 and hence a total flow rate ($Q_t$). A differential pressure measurement occurs at differential pressure step 404 using the Venturi-based meter 102. With reference to Equations 3-12 above, density step 406 calculates a mixture density ($\rho_m$) of the fluid flow 110 utilizing the differential pressure measurement from step 404 in combination with the flow velocity ($v_m$) from step 402.

At water content step 405, the WLR based meter 106 measures a water-in-liquid ratio (WLR). Next, liquid fraction determination step 408 calculates liquid content (liquid holdup, HL) using the mixture density ($\rho_m$) and the water-in-liquid ratio (WLR) according to:

$$HL = \frac{\rho_m - \rho_g}{(1-WLR)\rho_o + (WLR)\rho_w - \rho_g}. \quad \text{(Equation 20)}$$

For some embodiments, the liquid content (HL) may be measured directly with the WLR based meter 106 such as described in the previously incorporated U.S. Patent Publication No. 2006/0186340 and U.S. patent application Ser. No. 11/625,427 (WEAT/0641.P1). An output step 410 utilizes the liquid content (HL) and the water-in-liquid ratio (WLR) in Equations 15, 18 and 19 to calculate an oil flow rate ($Q_o$), a water flow rate ($Q_w$), and a gas-volume-fraction flow rate ($Q_g$).

Figure 5:
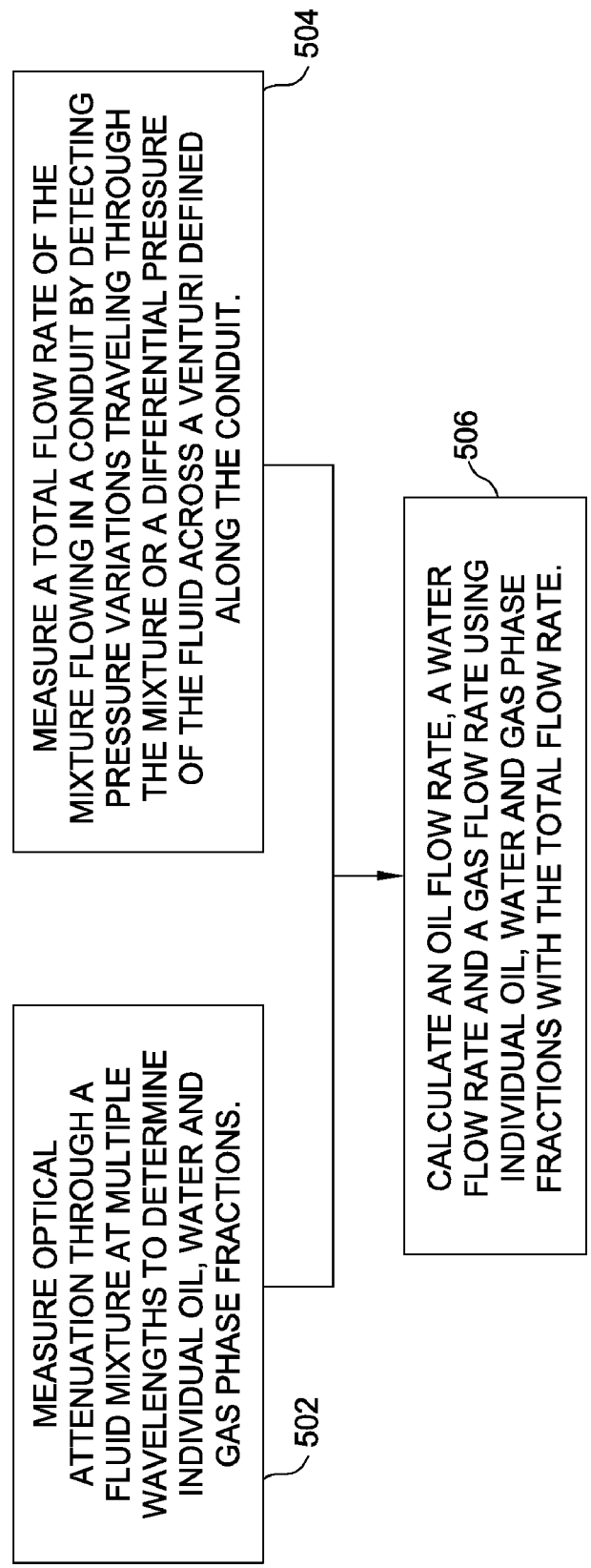
FIG. 5 is a flow chart illustrating use of the water-in-liquid ratio meter as a three phase fraction measuring device with at least one of the differential pressure based meter and the Sonar-based meter to calculate individual flow rates for gas, water and oil, according to embodiments of the invention.

FIG. 5 shows a flow chart illustrating use of the WLR meter 106 for three phase fraction measuring along with employment of at least one of the differential pressure based meter 102 and the Sonar-based meter 104 to calculate individual flow rates for gas, water, and oil. In addition to the following, U.S. patent application Ser. No. 11/382,761, which is herein incorporated by reference, describes an approach wherein a Sonar-based meter and a WLR meter measure flow. At phase fraction determination step 502, readings from the WLR meter 106 enable determination of individual oil, water and gas phase fractions. When the WLR meter 106 is spectroscopy based as previously described, absorbance measurements performed change as a function which may be defined, for example, as:

$$A_i = a_{oi}x_o + a_{wi}x_w + a_{gi}x_g + S \quad \text{(Equation 21)}$$

where $A_i$ is total absorbance at wavelength i and includes chemical (absorption) and physical (scattering) effects, $a_{oi}$, $a_{wi}$ and $a_{gi}$ are absorption coefficients for oil, water and gas respectively at wavelength i, $x_o$, $x_w$ and $x_g$ are pathlengths (and hence phase fractions) of oil, water, and gas respectively, and S is a scatter contribution (wavelength independent) to overall absorbance. Making four separate absorbance measurements for four different wavelengths enables solving for four unknowns ($x_o$, $x_w$, $x_g$ and S) in Equation 21.

In a total flow rate measurement step 504, one of either or both of the differential pressure based meter 102 and the Sonar-based meter 104 provide fluid pressure related data to enable determination of a total flow rate of the mixture. For example, Equations 1-4 illustrate use of the Sonar-based meter 104 to determine the total flow rate. The differential pressure based meter 102 relies on solving Equation 12 for the total flow rate with the mixture density determined by the respective phase fractions measured in the phase fraction determination step 502 and known corresponding individual densities. An output step 506 utilizes the individual phase fractions and the total flow rate to calculate an oil flow rate ($Q_o$), a water flow rate ($Q_w$) and a gas-volume-fraction flow rate ($Q_g$) based on the teachings herein.

The system 100 improves accuracy and certainty in the flow rate measurements as described heretofore due to unique aspects of each of the meters 102, 104, 106, which combine to provide sensitivity to certain measurement parameters and insensitivity to other parameters. For example, the WLR based meter 106 provides its results that are independent of GVF and flow rate. The Sonar-based meter 104 measures total volumetric flow rate independent of the WLR and GVF in wet-gas flows. Further, the Venturi-based meter 102 measures momentum dependent on volumetric flow rate and GVF but independent on WLR in wet-gas flows.

Providing multiple ways to utilize at the signal interface circuitry 112 the data received from the meters 102, 104, 106 establishes redundancy that can be beneficial for meter diagnostic purposes or in the event of failure of either the WLR based meter 106 or the Venturi-based meter 102 since options exist to make flow rate measurements using all the meters 102, 104, 106, the Venturi-based meter 102 and the Sonar-based meter 104, or the WLR based meter 106 and the Sonar-based meter 104. For example, a check of the meters 102, 104, 106 in a subsea application of the system 100 can occur utilizing this redundancy. Operation can proceed with functional ones of the meters 102, 104, 106 based on the outcome of such check.

In addition, certain types of flows may lend themselves to a particular configuration of the system 100 relative to other operational modes of the system 100. The Lockhart-Martinelli number describes the wetness of a wet-gas as provided in the following definition and typical values for different wet-gas types:

$$X = \frac{v_{SL}}{v_{Sg}} \cdot \sqrt{\frac{\rho_L}{\rho_g}} \Rightarrow \begin{cases} X \leq 0.02 & \Rightarrow \text{Wet gas Type 1} \\ 0.02 < X \leq 0.30 & \Rightarrow \text{Wet gas Type 2} \\ X > 0.3 & \Rightarrow \text{Wet gas Type 3} \end{cases}$$

where $v_{SL}$ and $v_{Sg}$ are superficial liquid and gas velocities, and $\rho_L$ and $\rho_g$ are liquid and gas densities, respectively. As the value of Lockhart-Martinelli number decreases, the flow approaches to a single-phase gas flow. Larger values refer to flows with increased liquid content. Analysis of the wet-gas types and the capabilities of the meters 102, 104, 106 reveals that when the flow is close to a single-phase gas flow (i.e., Wet-gas Type 1), the speed of sound measurements are expected to be excellent. In this case, one of the dual-configuration solutions (i.e., the Venturi-based meter 102 and the Sonar-based meter 104 or the WLR based meter 106 and the Sonar-based meter 104) can resolve the phase flow rates. When the liquid content is high (i.e., Wet-gas Type 3), the accuracy in the speed of sound measurements tends to decrease, meaning that a triple-configuration (all the meters 102, 104, 106) can be preferred to resolve all the phase flow rates or two phase flow rates can be determined with the combination of the Venturi-based meter 102 and the Sonar-based meter 104 (see, FIG. 2).

Ordering and placement of the meters 102, 104, 106 along the conduit 108 can change from the arrangement shown in FIG. 1 without departing from embodiments of the invention. For some embodiments, placement of the Sonar-based meter 102 along a reduced inner diameter section of the conduit 108 associated with a throat extension of the Venturi-based meter 102 facilitates measurements made with the Sonar-based meter 102 due to an increase in velocity at the reduced inner diameter section. Further, disposing the water-cut meter 106 downstream of the Venturi-based meter 102 can provide an advantage of mixing the fluid flow 110. In embodiments where the water cut meter 106 makes full bore spectral measurements, locating the water-cut meter 106 in the throat or throat extension of the Venturi-based meter 102 limits a path length analyzed, which aids in preventing saturation due to an excessive quantity of absorbing material within the path length.

Figure 6:
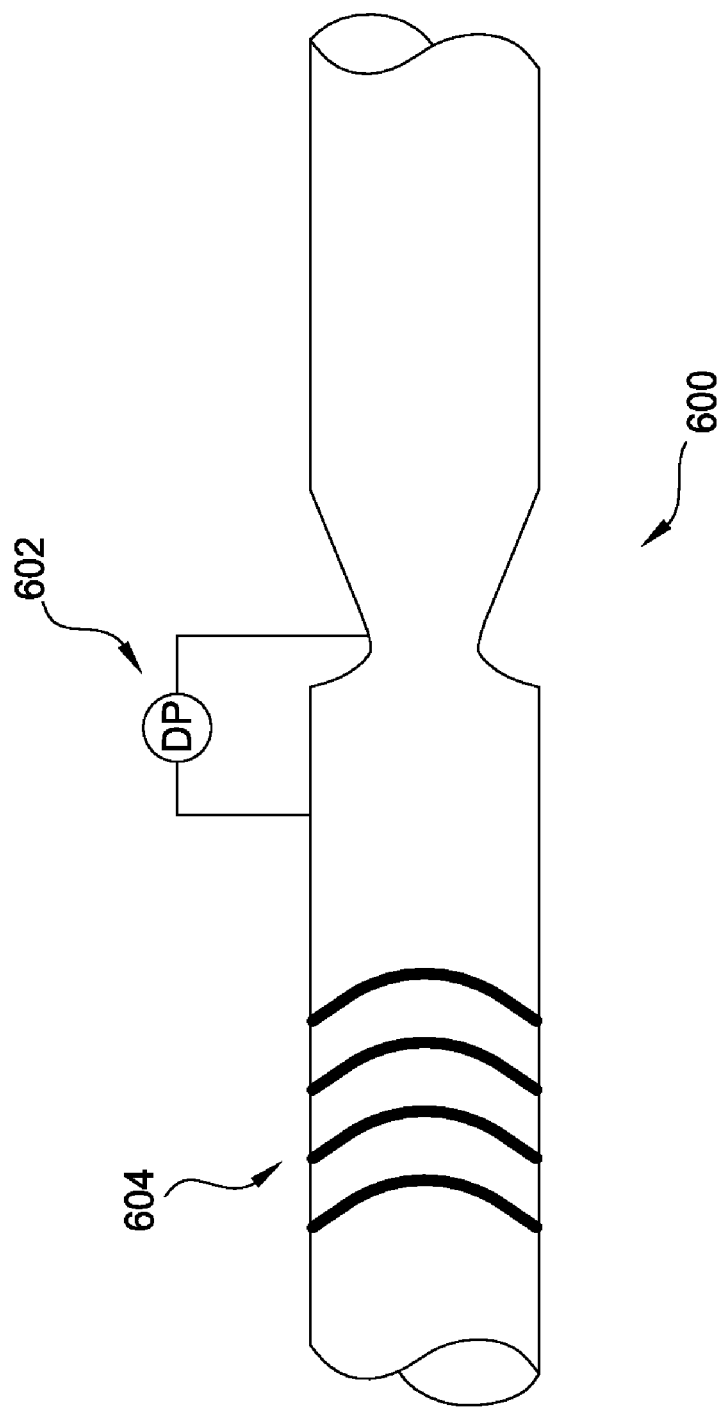
FIG. 6 is a view of an alternative flowmeter configuration suitable for applications shown in the flow charts of FIGS. 2 and 3.

FIG. 6 illustrates a flowmeter 600 having an exemplary alternative configuration representing one possible rearrangement of the system 100 shown in FIG. 1. The flowmeter 600 includes a pressure sensor array 604 and a Venturi differential pressure sensor 602. Therefore, the flowmeter 600 can operate based on applications shown in the flow charts of FIGS. 2 and 3 as described heretofore since the optional water cut meter is not present. Apparent modifications to the foregoing equations may be required with the flowmeter 600 to account for area differences where measurements are taken, for example, as a result of the rearrangement.

Figure 7:
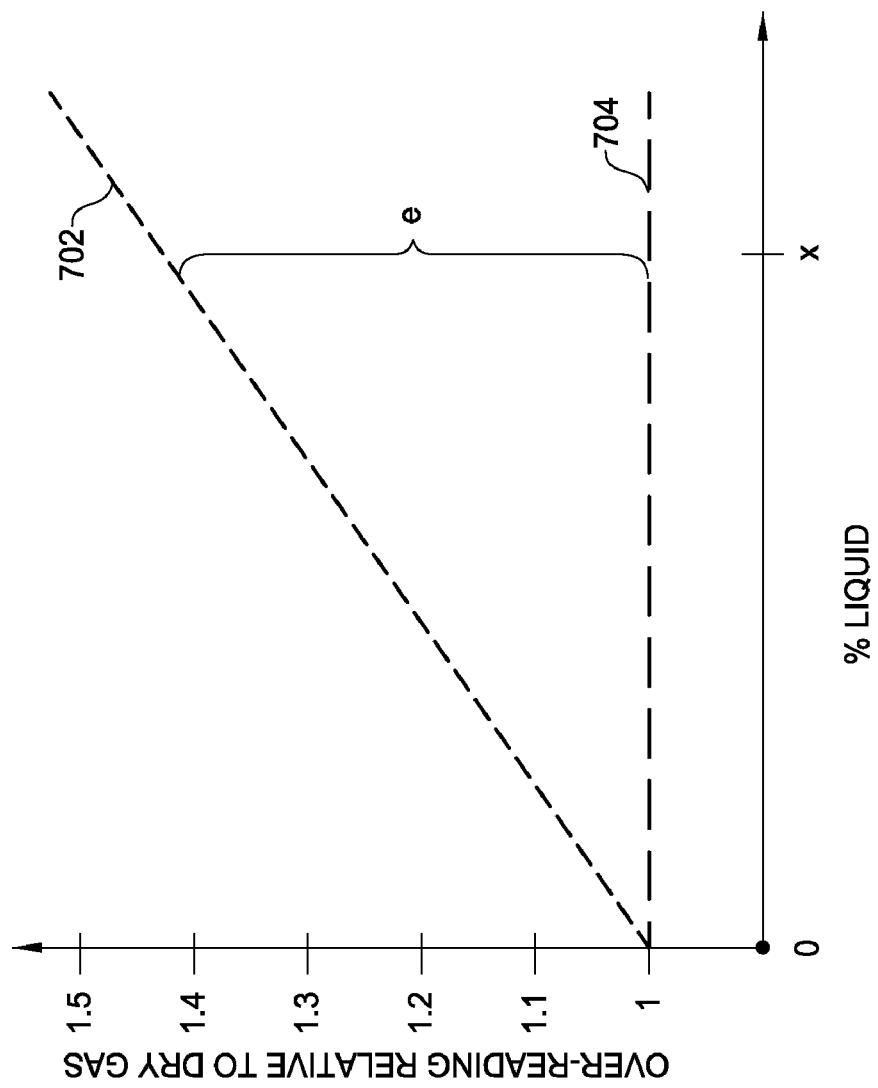
FIG. 7 is a graph of over-reading relative to dry gas versus liquid rate as determined with the differential pressure-based meter and the Sonar-based meter in order to graphically illustrate a liquid fraction capability.

FIG. 7 is a graph of percentage liquid versus an over-reading relative to dry gas defined as a measurement reading from a meter relative to a true or actual value for that parameter being measured. Line 702 fits flow rate data obtained with a differential pressure device measuring momentum for various percentages of liquid. This predictable over-reading that occurs using the differential pressure device results from liquid droplets affecting the momentum (or kinetic energy) of the flow due to their high relative mass compared to gas. Line 704 fits data gathered from a Sonar-based meter measuring flow velocity for various percentages of liquid. The line 704 follows close to the ratio of 1.0 indicating no substantial misreading. Further, a value for a difference in readings "e" correlates to a particular percentage "x" of liquid as exemplified with the foregoing algorithms described herein. The true or close to true reading from the Sonar-based meter in the presence of water ensures that the difference in readings "e" remains outside deviations of the meters to aid in improving accuracy and certainty.

While the Sonar-based meter 104 represents one type of flow velocity meter, other devices may be employed to measure flow velocity for utilization in some embodiments of the invention based on the foregoing description. For example, at least two optical sensors spatially distributed along a length of the conduit and designed to detect light interactions with the fluid mixture such that detected time-varying signals can be processed via cross-correlation or an array processing algorithm may provide desired flow velocity information. U.S. patent application Ser. No. 11/421,700, which is herein incorporated by reference, describes such an exemplary multiphase flowmeter.

While the foregoing is directed to embodiments of the present invention, other and further embodiments of the invention may be devised without departing from the basic scope thereof, and the scope thereof is determined by the claims that follow.

What is claimed is:

1. An apparatus for measuring flow of a fluid mixture in a conduit, comprising:
   a pressure sensor array based meter comprising an array of sensors that detect pressure variations traveling with the fluid mixture; and
   a water-in-liquid ratio meter configured to perform an infrared optical based spectroscopy analysis of the fluid mixture.

2. The apparatus of claim 1, wherein the spectroscopy analysis includes attenuation measurements of wavelength bands absorbed by water compared to attenuation of wavelength bands substantially transmitted through water.

3. The apparatus of claim 1, wherein the pressure sensor array based meter further detects acoustic pressure variations traveling at the speed of sound in the fluid mixture.

4. The apparatus of claim 1, wherein at least one of the sensors comprises a coil of optical fiber wrapped around the conduit.

5. An apparatus for measuring flow of a fluid mixture in a conduit, comprising:
   a differential pressure based meter configured to detect a differential pressure across a fluid flow pressure change inducing section along the conduit; and
   a water-in-liquid ratio meter configured to perform an infrared optical based spectroscopy analysis of the fluid mixture.

6. The apparatus of claim 5, wherein the spectroscopy analysis includes attenuation measurements of wavelength bands absorbed by water compared to attenuation of wavelength bands substantially transmitted through water.

7. The apparatus of claim 5, wherein the fluid flow pressure change inducing section comprises a flow nozzle.

8. The apparatus of claim 5, wherein the fluid flow pressure change inducing section comprises a flow nozzle formed by the conduit.

9. The apparatus of claim 5, wherein the fluid flow pressure change inducing section comprises an orifice plate or a V-cone.

10. The apparatus of claim 5, wherein an inner diameter of the conduit converges to a throat section in the fluid flow pressure change inducing section.

11. The apparatus of claim 10, wherein the water-in-liquid ratio meter is disposed at the throat section of the fluid flow pressure change inducing section.

12. The apparatus of claim 5, wherein the water-in-liquid ratio meter is disposed downstream of the differential pressure based meter.

13. An apparatus for measuring flow of a fluid mixture in a conduit, comprising:
   at least one of a flow velocity meter configured to sense along the conduit pressure variations traveling with the fluid mixture and a differential pressure based meter configured to sense a differential pressure across a fluid flow pressure change inducing section along the conduit;
   a water-in-liquid ratio meter configured to perform an infrared optical based spectroscopy analysis of the fluid mixture; and
   a processor configured with logic to determine a total flow rate from the at least one of the flow velocity meter and the differential pressure based meter, to determine one or more phase fractions based on the infrared optical based spectroscopy analysis, and to calculate one or more phase flow rates based on the phase fractions and the total flow rate.

14. The apparatus of claim 13, wherein the phase fractions comprise individual oil, gas, and water fractions and the phase flow rates comprise individual oil, gas, and water flow rates.

15. The apparatus of claim 13, wherein the fluid flow pressure change inducing section comprises a flow nozzle.

16. The apparatus of claim 13, wherein the fluid flow pressure change inducing section comprises a flow nozzle formed by the conduit.

17. The apparatus of claim 13, wherein the fluid flow pressure change inducing section comprises a Venturi.

18. The apparatus of claim 13, wherein an inner diameter of the conduit diverges in the fluid flow pressure change inducing section.

19. The apparatus of claim 13, wherein the flow velocity meter comprises an array of pressure sensing elements.

20. The apparatus of claim 19, wherein at least one of the pressure sensing elements comprises a coil of optical fiber wrapped around the conduit.

* * * * *